United States Patent [19]

Glaser

[11] Patent Number: 4,944,898

[45] Date of Patent: Jul. 31, 1990

[54] CEILING FAN BLADE MOUNTED AIR FRESHNER DISPENSING DEVICE

[76] Inventor: Stephen B. Glaser, 464 Division Ave., Hicksville, N.Y. 11801

[21] Appl. No.: 412,342

[22] Filed: Sep. 26, 1989

[51] Int. Cl.⁵ .............................................. B01F 3/04
[52] U.S. Cl. ...................................... 261/84; 422/124; 239/34; 239/60; 239/289; 261/DIG. 65
[58] Field of Search ........................... 261/84, DIG. 65; 422/124; 239/34, 60, 289

[56] References Cited

U.S. PATENT DOCUMENTS

| | | | |
|---|---|---|---|
| 2,262,772 | 11/1941 | Larsen | 261/DIG. 65 |
| 2,720,013 | 10/1955 | Clarke | 239/60 |
| 3,031,146 | 4/1962 | Albamonte | 239/60 |
| 3,844,478 | 10/1974 | Davis | 239/60 |
| 4,004,685 | 1/1977 | Mizuno et al. | 206/0.5 |
| 4,040,568 | 8/1977 | Mason, Jr. et al. | 239/60 |
| 4,208,012 | 6/1980 | Dutcher | 239/57 |
| 4,258,004 | 3/1981 | Valenzona et al. | 422/123 |
| 4,615,486 | 10/1986 | Konicek | 261/DIG. 65 |
| 4,666,670 | 5/1987 | Cox | 422/124 |
| 4,813,344 | 3/1989 | Greif | 422/124 |

Primary Examiner—Tim Miles
Attorney, Agent, or Firm—Terry M. Gernstein

[57] ABSTRACT

An air freshener dispensing device is mounted on the blade of a ceiling fan and includes channels that are shaped to increase the velocity of air relative to the air freshener product over the velocity of the air relative to the case in which the air freshener product is contained as the fan blade rotates. The case is releasably mounted on the fan blade so the product can be changed or replenished.

5 Claims, 1 Drawing Sheet

CEILING FAN BLADE MOUNTED AIR FRESHNER DISPENSING DEVICE

TECHNICAL FIELD OF THE INVENTION

The present invention relates to the general art of dispensing, and to the particular field of air fresheners.

BACKGROUND OF THE INVENTION

There are a myriad of odors associated with buildings and residences. Some of these odors, such as cooking odors, can be quite pleasant; whereas, others, such as smoking odors, can be quite unpleasant.

Accordingly, there are a variety of room freshening deodorant dispensing devices known in the art. These devices include simple sprays and wick-type dispensers, for example.

While somewhat effective in some circumstances, the deodorant devices similar to the above-mentioned devices have several drawbacks. For example, these devices are somewhat restricted in the amount of area that can be effectively treated, and could be limited to a particular portion of a single room. Furthermore, such devices can create a strong odor gradient that can be quite noticeable, and hence can be undesirable. An odor gradient has a very strong odor in an area adjacent to the dispenser and a very weak odor in an area spaced from that dispenser.

Other means for dispensing deodorant into a specified area include deodorant obtaining and dispensing filters for use in a central heating and cooling system. However, such devices may not be long lasting enough to be economically feasible, especially if the building has many rooms. Some rooms may require deodorizing, while others do not, yet such room selection is not possible using such centrally located deodorant dispensing means without cutting off a room from being heated or cooled, which may not be desirable. Furthermore, such devices may be expensive to install and replace.

Other means for dispensing deodorant into a room have included placing deodorant dispensing devices on the blades of a fan. Such devices have the advantage of wide dispersant plus room-specific characteristics. These devices have been placed on table fans as well as on ceiling fans.

While successful for their stated purpose, fan blade mounted room deodorant dispensers still have drawbacks. Specifically, the known devices do not take full advantage of the rapid movement thereof caused by being fixed to a rapidly moving fan blade. Therefore, these devices often are only slightly more effective than the stationary dispensers.

Therefore, there is a need for a fan-blade mounted room deodorant dispenser that is mounted on the blade of a ceiling fan and which is adapted to take advantage of the rapid movement thereof due to the rapid motion of the fan blade.

OBJECTS OF THE INVENTION

It is a main object of the present invention to provide a fan-blade mounted room deodorant dispenser.

It is another object of the present invention to provide a fan-blade mounted room deodorant dispenser that is mounted on the blade of a ceiling fan.

It is another object of the present invention to provide a fan-blade mounted room deodorant dispenser that is mounted on the blade of a ceiling fan and which is adapted to take advantage of the rapid movement thereof due to the rapid motion of the fan blade.

SUMMARY OF THE INVENTION

These, and other, objects are achieved by a fan-blade mounted room deodorant dispenser that is mounted on a blade of a ceiling fan and which includes specially slots through which room air contacts the deodorant. The slots are converging/ diverging in shape and will guide the air to increase its velocity relative to the deodorant dispensing element of the device. The converging/diverging shape will apply no matter which direction the fan blade is rotating, either clockwise or counterclockwise.

In this manner, the rapid velocity of the air relative to the dispenser will be increased over that relative velocity produced by fan blade rotation alone thereby enhancing the effect of the dispensing process. The fan-mounted dispenser thus will be more effective than prior fan-mounted dispensers yet will still retain the other advantages associated with ceiling fan-mounted air fresheners.

BRIEF DESCRIPTION OF THE DRAWING FIGURES

DETAILED DESCRIPTION OF THE PREFERRED EMBODIMENT OF THE INVENTION

Figure 1:
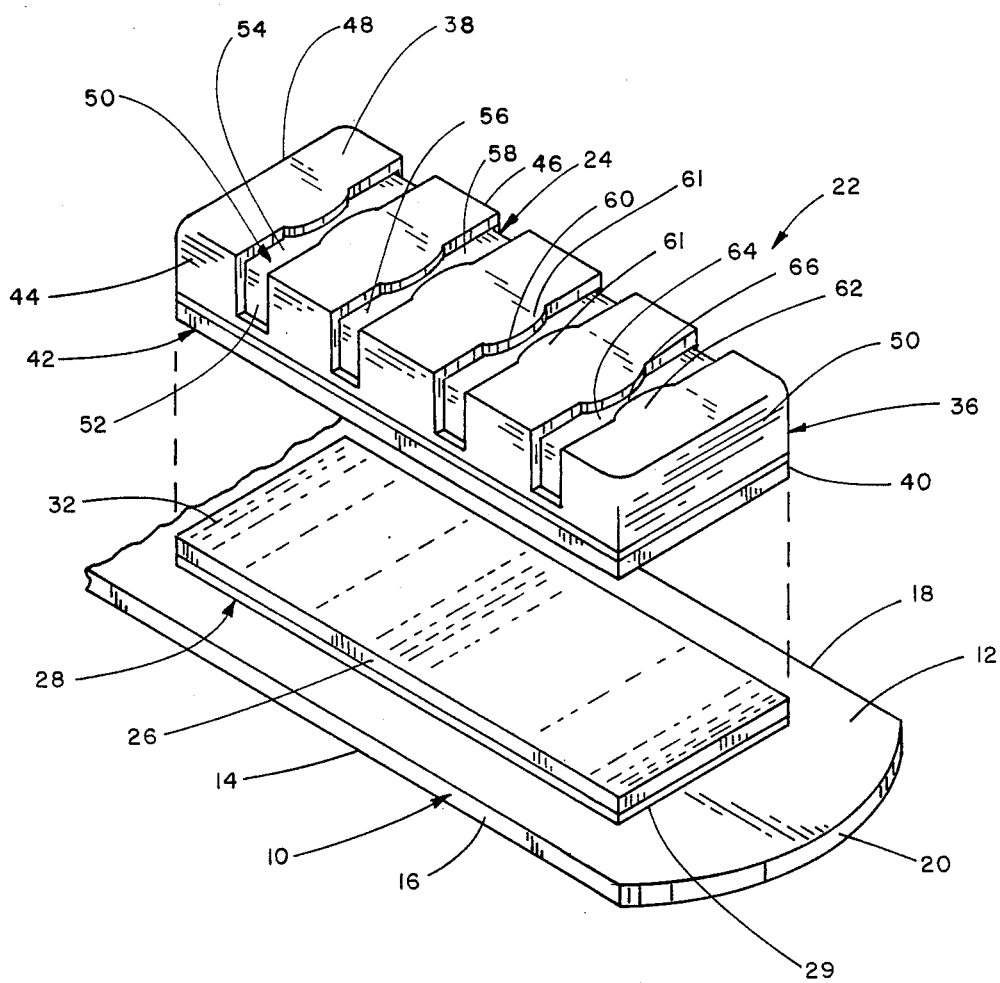
FIG. 1 is a perspective of the ceiling fan-mounted air freshener dispensing device of the present invention.

Shown in FIG. 1 is a ceiling fan blade 10 that is mounted on a ceiling fan (not shown) for rotation in either the clockwise or the counterclockwise direction. The fan blade 10 includes a planar top surface 12 and a bottom surface 14 and edges 16 and 18 all connected together by an arcuate end 20. The fan is used for its usual purpose of forcing air to flow in a chosen direction in a room.

An air freshening-product dispenser 22 is mounted on the fan blade top surface 12 to be contacted by air as the fan blade rotates. The air freshening product 24 is of the type that is dispensed due to such air-product contact, and can be a solid block that is replaceable when depleted.

The dispenser 22 includes a planar mounting element 26 fixed to the top surface of the fan blade. This mounting element includes a bottom surface 28 fixed to the blade surface as by adhesive 29 or the like, and a top surface 30 that includes a releasable mounting agent, such as hook-and-loop fastener means 32 or the like. The releasable mounting agent permits changing the deodorizing block.

The dispenser further includes a hollow case 36 which contains the air freshening product 24 and which mounts that product to the fan blade via the mounting element 26. The case 36 includes a top surface 38, a planar bottom surface 40 which includes a releasable mounting means, such as a hook-and-loop fastener means 42, that co-operates with the releasable mounting agent on the mounting element to releasably fix the case to the fan blade. The case 36 further includes side surfaces 44 and 46 and end surfaces 48 and 50.

The case is releseably attached to the bottom element so that it can be opened to remove and insert various products 24.

The dispenser 22 includes a means for increasing the relative velocity of the air passing by the product 24 over that relative velocity existing between the case and the air as the fan blade 10 rotates. This increase in relative velocity will increase the effectiveness of the dispenser 22, and is designed to work no matter whether the fan blade rotates clockwise or counterclockwise.

The relative air velocity increasing means operates on the principle of the converging/diverging nozzle. Such nozzle theory is fully discussed in textbooks such as "Rocket Propulsion Elements" by G.A. Sutton, and published by John Wiley and Sons in 1963, and "Rocket Propulsion" by M. Barrere, et al, published by Elsevier Publishing Company in 1960, the disclosures of which are incorporated herein by reference.

The means includes a plurality of channels or slots, such as slot 50 defined in the case to expose the product 24 to the air. Each of the slots includes a first portion 52 which defines a side channel on each side 44 and 46 of the case, and a second portion 54 which defines a second channel on the top 38 of the case. The second portion 54 is further divided into entrance/exit portions 56 and 58 and a central throat portion 60. The portions 52, 56 and 58 are all straight in shape, while the central throat section is formed by two opposed arcuate projection elements 61 to be curved as will be discussed below.

The throat section is shaped to define a section that converges towards the center of the slot from each end thereof. Thus, the central section has a converging section 62 and a converging section 64 on each end thereof, and a narrow neck 66 at the center of the slot. When the fan blade is rotating, one of these sections is converging and the other is diverging with respect to air passing through the slot so the central section acts in the manner of a converging/diverging nozzle with respect to the air flowing in contact with the product in the slots 50. The shape of the central section can be selected to operate with equal efficiency when the blade rotates in either the clockwise or the counterclockwise direction, or it can be designed to be more efficient when the blade rotates in one or the other direction. For example, if the blade will be used primarily as a cooling element, and will rotate in the clockwise direction most of the time, the central section can be designed to be more efficient when air is flowing over the product and through the slots in, for example, from right to left, or vice versa.

Figure 2:
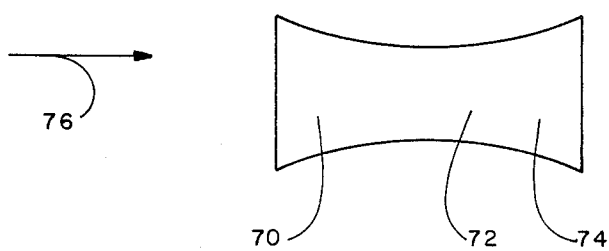
FIG. 2 is a schematic of a De Laval-like nozzle shape used in the dispenser of the present invention to increase the velocity of the air relative to the dispenser.

A suitable shape for the slots is shown in FIG. 2 as being similar to the cross-sectional shape of a De Laval-type nozzle. This shape may be more efficient in one direction than in another as discussed above, and includes a converging entrance section 70, a throat section 72 and a diverging exit section 74 for air flowing therethrough in the direction indicated in FIG. 2 by the arrow 76.

It is understood that while certain forms of the present invention have been illustrated and described herein, it is not to be limited to the specific forms or arrangements of parts described and shown.

I claim:

1. A ceiling fan blade mounted room deodorant and air freshening product dispenser comprising:
    (A) a planar mounting element having adhesive on one surface thereof for attaching said mounting element to a planar surface of a ceiling fan blade and a hook-and-loop fastening means on another surface thereof;
    (B) a hollow case containing air freshener product therein and having a planar base with hook-and-loop fastening elements thereon which co-operate with the hook-and-loop fastening means on said mounting element to releasably hold said case on said fan blade, a top surface, side surfaces and end surfaces connected to said planar base; and
    (C) an air flow control means for increasing the air velocity relative to said air freshener product over the air velocity relative to said case as said fan blade rotates, said air flow control means including a channel defined in said case top surface and a converging/diverging section in said channel.

2. The product dispenser defined in claim 1 wherein said air flow control means includes two opposed arcuate projections in said channel that are positioned to define a throat section in said channel.

3. The product dispenser defined in claim 2 wherein said converging/diverging section is in the shape of a De Laval-type nozzle cross-sectional shape.

4. The product dispenser defined in claim 3 wherein said air flow control means further includes a plurality of channels.

5. The product dispenser defined in claim 4 wherein each channel further includes a portion on each side of said case.

* * * * *